US012599071B2

(12) United States Patent
Hsieh et al.

(10) Patent No.: US 12,599,071 B2
(45) Date of Patent: Apr. 14, 2026

(54) METHODS FOR INCREASING CHROMIUM IN WHITE KIDNEY BEANS

(71) Applicant: Hansford Biotech Co., Ltd., Kaohsiung City (TW)

(72) Inventors: Wei Ting Hsieh, Taichung City (TW); Kang-Ting Liao, Taichung City (TW); Ting-Yu Huang, Taichung City (TW)

(73) Assignee: Hansford Biotech Co., Ltd., Kaohsiung (TW)

( * ) Notice: Subject to any disclaimer, the term of this patent is extended or adjusted under 35 U.S.C. 154(b) by 247 days.

(21) Appl. No.: 18/420,962

(22) Filed: Jan. 24, 2024

(65) Prior Publication Data

US 2025/0234828 A1     Jul. 24, 2025

(51) Int. Cl.
| | |
|---|---|
| *A01H 3/04* | (2006.01) |
| *A01C 1/06* | (2006.01) |
| *A01G 22/40* | (2018.01) |
| *C05B 1/02* | (2006.01) |
| *C05B 7/00* | (2006.01) |
| *C05C 9/00* | (2006.01) |
| *C05D 9/02* | (2006.01) |
| *C05F 3/00* | (2006.01) |
| *C05F 11/00* | (2006.01) |

(52) U.S. Cl.
CPC ................. *A01H 3/04* (2013.01); *A01C 1/06* (2013.01); *A01G 22/40* (2018.02); *C05B 1/02* (2013.01); *C05B 7/00* (2013.01); *C05C 9/00* (2013.01); *C05D 9/02* (2013.01); *C05F 3/00* (2013.01); *C05F 11/00* (2013.01)

(58) Field of Classification Search
None
See application file for complete search history.

(56) References Cited

FOREIGN PATENT DOCUMENTS

CN         106717685 A  *  5/2017  ........... A01C 21/005

OTHER PUBLICATIONS

Brown, Brad, and Dale Westermann. "Soil fertility and bean production." Bean production, research and utilization: Proceedings of the Idaho Bean Workshop, edited by Singh, SP. vol. 75. 2000; (Year: 2000).*
Lazicki, Patricia, et al., "Dry Bean Production in California", available online at https://apps1.cdfa.ca.gov/FertilizerResearch/docs/Bean_Production_CA.pdf . (Year: 2016).*

* cited by examiner

*Primary Examiner* — Weihua Fan
(74) *Attorney, Agent, or Firm* — Studebaker Brackett PLLC

(57)     ABSTRACT

The present invention discloses methods for increasing chromium in white kidney bean. The method comprises preparing field, performing a first treatment to the seeds of the white kidney bean, performing a second treatment during the seeding period, performing a third treatment during the flowering period, performing a fourth treatment during the fruiting period and performing a fifth treatment during the maturing period. Meanwhile, the amount of chromium in the white kidney bean produced according to the present invention is from 400 to 800 μg/kg.

18 Claims, 1 Drawing Sheet

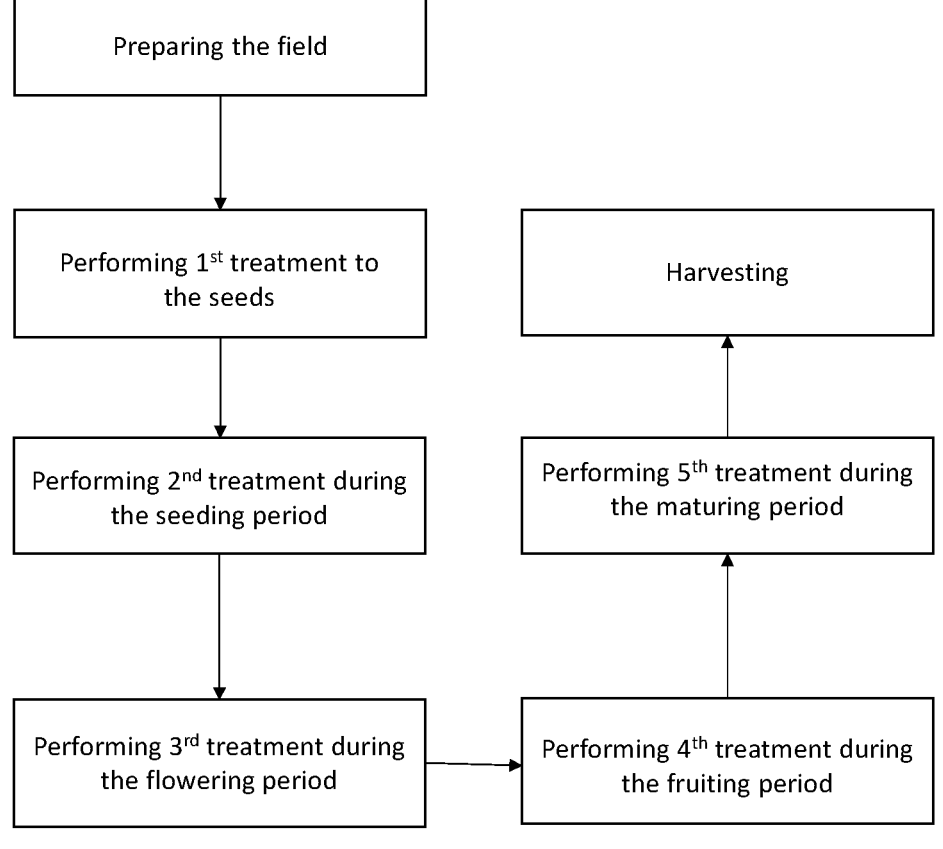

METHODS FOR INCREASING CHROMIUM IN WHITE KIDNEY BEANS

FIELD OF THE INVENTION

The present invention relates to methods for planting white kidney beans, in particular to a method for increasing the amount of chromium in the white kidney beans.

BACKGROUND OF THE INVENTION

White kidney beans, with a white appearance, originated in the Americas, particularly in Mexico and Argentina, belong to the legume family under the genus *Phaseolus*. Through artificial cultivation, they have adapted to humid and cold high-altitude regions. In terms of nutritional value, white kidney beans are rich in α-amylase inhibitors and dietary fiber. They effectively block the intake of starch calories, reducing the body's fat sources. Additionally, white kidney beans induce a feeling of satiety, ensuring the absorption of other essential nutrients while reducing fat and calorie intake. The beans themselves possess significant nutritional value, containing abundant proteins, carotenoids, calcium, phosphorus, iron, and vitamins. Due to their plump grains, delicate texture, and rich nutrients, white kidney beans are widely used as a staple food or side dish.

Organic chromium is an essential trace element for the human body. It participates in the synthesis of various organic chromium enzymes and proteins within the body. Notably, it is involved in the formation of glutathione peroxidase, a catalyst in organisms that converts hydrogen peroxide or lipid peroxides into water or various alcohols. This process eliminates free radical attacks on biological membranes, protecting them from oxidative damage. Organic chromium also plays a role in the composition of thyroid iodide peroxidase. It enhances the immune system, promoting the proliferation of lymphocytes and the synthesis of antibodies and immunoglobulins. Organic chromium exhibits a significant inhibitory and protective effect against various cancers such as colon cancer, skin cancer, liver cancer, and breast cancer. Its intermediate metabolite, methyl enol, demonstrates strong anti-cancer activity. Additionally, organic chromium synergizes with nutrients such as vitamin E, allicin, linoleic acid, germanium, zinc, and others to increase antioxidant activity. Moreover, organic chromium has a role in alleviating and mitigating the toxicity of heavy metals.

Although white kidney beans contain excellent nutrition, their organic chromium content is insufficient, and there is currently a lack of health products with enriched chromium white kidney bean extracts in the market. Therefore, there is a need to provide a cultivation method to increase the amount of chromium in white kidney beans. Additionally, the method addressing this need should be scalable for industrial use.

SUMMARY OF THE INVENTION

Accordingly, in the first aspect of the present invention provides a method for increasing chromium in white kidney bean. The method comprises following steps as preparing field, performing a first treatment to the seeds of the white kidney bean, performing a second treatment during the seeding period of the white kidney bean, performing a third treatment during the flowering period of the white kidney bean, performing a fourth treatment during the fruiting period of the white kidney bean and performing a fifth treatment during the maturing period of the white kidney bean. The preparing field may further include loosing the field, applying organic fertilizer, then harrowing the field, and creating ridges with a trench depth from 10 to 30 cm, trench width from 1.5 to 2.5 m, and ridge width of 1 to 2 m.

Moreover, the first treatment may further include immersing the seeds in a slurry and adding a protective agent. The second treatment may further include spraying a first solution having 12-185 kg/hectare (i.e., 11-165 pound/acre or 5-75 kg/acre) of diammonium phosphate, 2.4-124 kg/hectare (i.e., 2.2-110 pound/acre or 1-50 kg/acre) of calcium superphosphate, 25-185 kg/hectare (i.e., 22-165 pound/acre or 10-75 kg/acre) of urea, 10 to 30 ppm chromium (III) chloride and 0.25-25 kg/hectare (i.e., 0.22-22 pound/acre or 0.1-10 kg/acre) of zinc sulfate. The third treatment may further include spraying a second solution having 1.2-62 kg/hectare (i.e., 1.1-55 pound/acre or 0.5-25 kg/acre) of dipotassium phosphate, 1.2-49 kg/hectare (i.e., 1.1-44 pound/acre or 0.5-20 kg/acre) of zinc sulfate, 0.12-12 kg/hectare (i.e., 0.11-11 pound/acre or 0.05-5 kg/acre) of salicylic acid, and 0.12-12 kg/hectare (i.e., 0.11-11 pound/acre or 0.05-5 kg/acre) of chlorogenic acid. The fourth treatment may further include spraying a third solution having 0.32-32 kg/hectare (i.e., 0.29-29 pound/acre or 0.13-13 kg/acre) of salicylic acid, 0.32-32 kg/hectare (i.e., 0.29-29 pound/acre or 0.13-13 kg/acre) of chlorogenic acid, and 1.2-49 kg/hectare (i.e., 1.1-44 pound/acre or 0.5-20 kg/acre) of zinc sulfate, and the fifth treatment may further include spraying a fourth solution having 0.32-7.4 kg/hectare (i.e., 0.29-6.6 pound/acre or 0.13-3 kg/acre) of salicylic acid and 0.32-7.4 kg/hectare (i.e., 0.29-6.6 pound/acre or 0.13-3 kg/acre) of chlorogenic acid.

In one embodiment of the present invention, the seeds may be further exposed to the sun for 1 to 2 days before performing the first treatment.

In one embodiment of the present invention, the amount of organic fertilizer applied to the field is approximately from 3 to 6 kg/m².

In one embodiment of the present invention, the organic fertilizer is selected from plant ash, compost, animal manure, turf or combination thereof.

In one embodiment of the present invention, the animal manure may further include cow manure, sheep manure, and chicken manure in a weight ratio of 5:3:2, and be mixed uniformly and matured for approximately from 60 to 120 days before use.

In one embodiment of the present invention, the mass ratio of the seeds to the slurry is approximately from 1:0.1 to 0.8.

In one embodiment of the present invention, the mass ratio of the seeds to the protective agent is approximately from 1:0.02 to 0.1

In one embodiment of the present invention, the slurry is selected from albic soil, kaolin soil, yellow soil, red soil, clay soil, or combination thereof.

In one embodiment of the present invention, the protective agent includes a wettable powder and a seed coating agent.

In one embodiment of the present invention, the wettable powder and the seed coating agent are mixed in a mass ratio of 1:1 to 2.

In one embodiment of the present invention, the wettable powder further includes a carrier and a supportive agent.

In one embodiment of the present invention, the carrier is selected from diatomaceous earth, pottery clay, kaolin clay, albic soil, peat, lightweight calcium carbonate, silica, white carbon black or combination thereof.

In one embodiment of the present invention, the supportive agent is selected from saponin, anion surfactant, washing powder, sodium dodecyl sulfonate, sodium lignosulphonate, carboxymethyl cellulose, polyvinyl alcohol, polyethylene glycol, sodium tripolyphosphate, sodium hexametaphosphate or combination thereof.

In one embodiment of the present invention, the second solution may further include chromium(III) chloride having the concentration approximately from 50 to 100 ppm.

In one embodiment of the present invention, the third solution may further include chromium(III) chloride having the concentration approximately from 50 to 100 ppm.

In one embodiment of the present invention, the fourth solution may further include chromium (III) chloride having the concentration approximately from 100 to 300 ppm.

In one embodiment of the present invention, the amount of the chromium content of the white kidney bean is approximately from 400 to 800 μg/kg.

BRIEF DESCRIPTION OF THE DRAWINGS

Embodiments of the invention are described in more details hereinafter with reference to the drawings, in which:

The FIGURE depicts the flow chart of planting method for increasing the amount of chromium in the white kidney beans.

DEFINITIONS

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

DETAILED DESCRIPTION

In the following description, it will be apparent to those skilled in the art that modifications, including additions and/or substitutions may be made without departing from the scope and the spirit of the invention. Specific details may be omitted so as not to obscure the invention; however, the disclosure is written to enable one skilled in the art to practice the teachings herein without undue experimentation.

Provided herein are methods for increasing the amount of chromium in the white kidney beans as shown in the FIGURE. The methods include providing various concentration of chromium from seed preparation to the different growth phases such as seeding period, flowering period, fruiting period, maturing period and harvesting phase of the white kidney beans. The cultivation method of the present invention, due to its use of biological transformation, converts inorganic chromium into organic chromium, which accumulates in the white kidney beans. Therefore, the present invention provides a natural resource of organic chromium including but not limited to chromium picolinate and chromium nicotinate. This organic chromium derived from white kidney beans, compared to existing artificially synthesized yeast organic chromium, has higher purity, fewer impurities, significantly improved biological utilization, and a good taste without any odor. It can be used in medical and health food. At the same time, because the cultivation method and production equipment of the present invention have low requirements, simple operation, short production cycle, and scalable production, the production cost is relatively low. The development and utilization of the present invention will generate good social and economic benefits.

More specifically, the method in the present invention includes following steps:

(1) Field preparation: the preparing field may further include loosing the field, applying organic fertilizer, then harrowing the field, and creating ridges with a trench depth approximately from 10 to 30 cm, trench width from 1.5 to 2.5 m, and ridge width of 1 to 2 m.

(2) Seed treatment: the seed treatment may include pouring the seeds into a sticky slurry, ensuring that the seeds are evenly coated with the sticky slurry. Slowly add a protective agent while simultaneously stirring the seeds slowly until they can separate on their own.

(3) Seeding period: performing a treatment during the seeding period by spraying a solution having 12 to 185 kg/hectare (i.e., 11 to 165 pound/acre or 5 to 75 kg/acre) of diammonium phosphate, 2.4 to 124 kg/hectare (i.e., 2.2 to 110 pound/acre or 1 to 50 kg/acre) of calcium superphosphate, 25 to 185 kg/hectare (i.e., 22 to 165 pound/acre or 10 to 75 kg/acre) of urea, 10 to 30 ppm chromium (III) chloride and 0.25 to 25 kg/hectare (i.e., 0.22 to 22 pound/acre or 0.1 to 10 kg/acre) of zinc sulfate.

(4) Flowering period: performing a treatment during the flowering period by spraying a solution having 1.2 to 62 kg/hectare (i.e., 1.1 to 55 pound/acre or 0.5 to 25 kg/acre) of dipotassium phosphate, 1.2 to 49 kg/hectare (i.e., 1.1 to 44 pound/acre or 0.5 to 20 kg/acre) of zinc sulfate, 0.12 to 12 kg/hectare (i.e., 0.11 to 11 pound/acre or 0.05 to 5 kg/acre) of salicylic acid, and 0.12 to 12 kg/hectare (i.e., 0.11 to 11 pound/acre or 0.05 to 5 kg/acre) of chlorogenic acid.

(5) Fruiting period: performing a treatment during the fruiting period by spraying a solution having 0.32 to 32 kg/hectare (i.e., 0.29 to 29 pound/acre or 0.13 to 13 kg/acre) of salicylic acid, 0.32 to 32 kg/hectare (i.e., 0.29 to 29 pound/acre or 0.13 to 13 kg/acre) of chlorogenic acid, and 1.2 to 49 kg/hectare (i.e., 1.1 to 44 pound/acre or 0.5 to 20 kg/acre) of zinc sulfate.

(6) Maturing and harvesting period: performing a treatment during the maturing period by spraying a solution having 0.32 to 7.4 kg/hectare (i.e., 0.29 to 6.6 pound/acre or 0.13 to 3 kg/acre) of salicylic acid and 0.32 to 7.4 kg/hectare (i.e., 0.29 to 6.6 pound/acre or 0.13 to 3 kg/acre) of chlorogenic acid.

To increase the productivity of the white kidney beans as well as the amount of the chromium, some steps or parameters have been taken or considered before the field preparation and seed treatment. First, some preceding crops such as potatoes, buckwheat, wheat, or corn may be planting before field preparation to increase the field fertility or mitigate insect damage. Second, the cultivation site is fallow land, with a soil pH range of 6 to 7, and the soil fertility is medium to high. Third, the seeds are selected as large, plump, well-organized, uniform in glossiness, free from pests and diseases, and undamaged, and the seeds may be further exposed to the sun for 1 to 2 days to eliminate potential bacteria or fungus infection during the growth of the white kidney beans before performing the seed treatment. Meanwhile, in some embodiments, the organic fertilizer may be selected for example but not limited to plant ash, compost, animal manure, or turf and the amount of organic fertilizer may be applied to the field in a concentration approximately from 3 to 6 $kg/m^2$ (for example, 3.5 $kg/m^2$, 4.5 $kg/m^2$, 5.5 $kg/m^2$, etc.), where the animal manure may further include cow manure, sheep manure, and chicken manure in a weight ratio of 5:3:2 (for example, in a weight ratio of 5.5:2.5:2 and 5:2.5:2.5 etc.), and be mixed uniformly and matured for approximately from 60 to 120 days before use.

In the present invention, a layer of sticky slurry is applied to coat the seeds to protect the seeds, and enhances the encapsulation effect of the protective agent. The slurry may prevent the loss of the protective agent due to changes in natural environmental conditions, not affecting the normal germination of the seeds, and it also effectively ensures the isolation of viruses, thereby increasing the seedling emergence rate and promoting uniform seedling emergence. The slurry in the present invention is for example but not limited to albic soil, kaolin soil, yellow soil, red soil, or clay soil. In some embodiments, the mass ratio of the seeds to the slurry is approximately from 1:0.1 to 0.8 (for example, 1:0.3, 1:0.5, and 1:0.7 etc.). The protective agent includes a wettable powder and a seed coating agent, where the wettable powder and the seed coating agent are mixed evenly in a mass ratio of 1:1 to 2 (for example, 1:1.2, 1:1.4, 1:1.6, and 1:1.8 etc.) before use. In some embodiments, the mass ratio of the seeds to the protective agent is approximately from 1:0.02 to 0.1 (for example, 1:0.04, 1:0.06, and 1:0.08, etc.). In addition, the wettable powder may further includes a carrier and a supportive agent, where the carrier is for example but not limited to diatomaceous earth, pottery clay, kaolin clay, albic soil, peat, lightweight calcium carbonate, silica, white carbon black and the supportive agent is for example but not limited to saponin, anion surfactant, washing powder, sodium dodecyl sulfonate, sodium lignosulphonate, carboxymethyl cellulose, polyvinyl alcohol, polyethylene glycol, sodium tripolyphosphate, sodium hexametaphosphate.

When white kidney bean plants reach a height of 20 to 40 cm with 5 to 7 leaves during the seeding period, a spray treatment is applied using a solution prepared by mixing 12 to 185 kg/hectare (i.e., 11 to 165 pound/acre or 5 to 75 kg/acre) of diammonium phosphate, 2.4 to 124 kg/hectare (i.e., 2.2 to 110 pound/acre or 1 to 50 kg/acre) of calcium superphosphate, 25 to 185 kg/hectare (i.e., 22 to 165 pound/ acre or 10 to 75 kg/acre) of urea, 10 to 30 ppm chromium (III) chloride and 0.25 to 25 kg/hectare (i.e., 0.22 to 22 pound/acre or 0.1 to 10 kg/acre) of zinc sulfate with 100 to 500 kg of water. In some embodiments, the preferable parts to apply the solution during the seeding period are roots and leaves of white kidney beans. During the flowering period of white kidney beans, a spray treatment is applied using a solution prepared by mixing 1.2 to 62 kg/hectare (i.e., 1.1 to 55 pound/acre or 0.5 to 25 kg/acre) of dipotassium phosphate, 1.2 to 49 kg/hectare (i.e., 1.1 to 44 pound/acre or 0.5 to 20 kg/acre) of zinc sulfate, 0.12 to 12 kg/hectare (i.e., 0.11 to 11 pound/acre or 0.05 to 5 kg/acre) of salicylic acid, 50 to 100 ppm chromium (III) chloride and 0.12 to 12 kg/hectare (i.e., 0.11 to 11 pound/acre or 0.05 to 5 kg/acre) of chlorogenic acid with 100 to 500 kg of water. In some embodiments, the preferable parts to apply the solution during the flowering period are flowers and leaves of white kidney beans. During the fruiting period of white kidney beans, a spray treatment is applied using a solution prepared by mixing 0.32 to 32 kg/hectare (i.e., 0.29 to 29 pound/acre or 0.13 to 13 kg/acre) of salicylic acid, 0.32 to 32 kg/hectare (i.e., 0.29 to 29 pound/acre or 0.13 to 13 kg/acre) of chlorogenic acid, 50 to 100 ppm chromium (III) chloride and 1.2 to 49 kg/hectare (i.e., 1.1 to 44 pound/acre or 0.5 to 20 kg/acre) of zinc sulfate. In some embodiments, the preferable parts to apply the solution during the fruiting period are leaves and pods of white kidney beans. During the maturing and harvesting period of white kidney beans, a spray treatment is applied using a solution prepared by mixing 0.32 to 7.4 kg/hectare (i.e., 0.29 to 6.6 pound/acre or 0.13 to 3 kg/acre) of salicylic acid, 100 to 300 ppm chromium (III) chloride and 0.32 to 7.4 kg/hectare (i.e., 0.29 to 6.6 pound/ acre or 0.13 to 3 kg/acre) of chlorogenic acid. In some embodiments, the preferable parts to apply the solution during these periods are leaves and pods of white kidney beans. After the harvest, the amount of the chromium content of the white kidney bean is from 400 to 800 µg/kg (for example, 500 µg/kg, 600 µg/kg, 700 µg/kg, etc.)

Example 1

Cultivation method for increasing the chromium in white kidney beans, comprising the following steps:
- (1) Field preparation: begin by deep plowing the planting field to a depth of 25 cm, incorporating 3.8 kg/m2 of organic fertilizer during the deep plowing. Then, finely rake and level the planting field. Create ridges with a trench depth of 15 cm, a trench width of 2 m, and a ridge width of 1 m. The plant ash and animal manure have been used as organic fertilizer, where the animal manure includes cow manure, sheep manure, and chicken manure in a weight ratio of 5:2.5:2.5, and be mixed uniformly and matured for 80 days before use.
- (2) Seed treatment: pour the seeds into a clay soil slurry, ensuring even coating, then slowly add a protective agent while stirring until the seeds can separate on their own. The mass ratio of seeds, slurry, and protective agent is 1:0.1:0.02. Plant the seeds with a depth of 1.5 cm, spacing rows 20 cm apart, and sowing 2 seeds per hole.
- (3) Seeding period: when the plants reach a height of 20 to 40 cm, a root and foliar spray treatment is applied using a dispersed solution. The solution is prepared by dissolving the following combination in 247 kg/hectare (i.e., 220 pound/acre or 100 kg/acre) of water: 12 kg/hectare (i.e., 11 pound/acre or 5 kg/acre) of diammonium phosphate, 2.4 kg/hectare (i.e., 2.2 pound/acre or 1 kg/acre) of calcium superphosphate, 25 kg/hectare (i.e., 22 pound/acre or 10 kg/acre) of urea, 20 ppm chromium (III) chloride and 1.2 kg/hectare (i.e., 1.1 pound/acre or 0.5 kg/acre) of zinc sulfate.
- (4) Flowering period: apply a spray treatment to the leaves and flowers using a dispersed solution prepared by dissolving the following combination in 247 kg/hectare (i.e., 220 pound/acre or 100 kg/acre) of water: 1.2 kg/hectare (i.e., 1.1 pound/acre or 0.5 kg/acre) of dipotassium phosphate, 1.2 kg/hectare (i.e., 1.1 pound/acre or 0.5 kg/acre) of zinc sulfate, 0.12 kg/hectare (i.e., 0.11 pound/acre or 0.05 kg/acre) of salicylic acid, 50 ppm chromium (III) chloride and 0.12 kg/hectare (i.e., 0.11 pound/acre or 0.05 kg/acre) of chlorogenic acid.

(5) Fruiting period: apply a spray treatment to the leaves and pods using a dispersed solution prepared by dissolving the following combination in 247 kg/hectare (i.e., 220 pound/acre or 100 kg/acre) of water: 0.32 kg/hectare (i.e., 0.29 pound/acre or 0.13 kg/acre) of salicylic acid, 0.32 kg/hectare (i.e., 0.29 pound/acre or 0.13 kg/acre) of chlorogenic acid, 50 ppm chromium (III) chloride and 1.2 kg/hectare (i.e., 1.1 pound/acre or 0.5 kg/acre) of zinc sulfate.

(6) Maturing and before harvest: when the pods begin to change color from green to yellow, 3-7 days before harvesting, apply a spray treatment to the leaves and pods using a dispersed solution prepared by dissolving the following combination in 247 kg/hectare (i.e., 220 pound/acre or 100 kg/acre) of water: 0.32 kg/hectare (i.e., 0.29 pound/acre or 0.13 kg/acre) of salicylic acid, 0.32 kg/hectare (i.e., 0.29 pound/acre or 0.13 kg/acre) of chlorogenic acid, 100 ppm chromium (III) chloride and 1.2 kg/hectare (i.e., 1.1 pound/acre or 0.5 kg/acre) of zinc sulfate.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. A method for increasing chromium in white kidney bean comprising:

preparing field including loosening the field, applying organic fertilizer, then harrowing the field, and creating ridges with a trench depth approximately from 10 to 30 cm, trench width from 1.5 to 2.5 m, and ridge width of 1 to 2 m;

performing a first treatment to the seeds of the white kidney bean including immersing the seeds in a slurry and adding a protective agent;

performing a second treatment during the seeding period of the white kidney bean including spraying a first solution having 12-185 kg/hectare of diammonium phosphate, 2.4-124 kg/hectare of calcium superphosphate, 25-185 kg/hectare of urea, 10 to 30 ppm chromium (III) chloride and 0.25-25 kg/hectare of zinc sulfate;

performing a third treatment during the flowering period of the white kidney bean including spraying a second solution having 1.2-62 kg/hectare of dipotassium phosphate, 1.2-49 kg/hectare of zinc sulfate, 0.12-12 kg/hectare of salicylic acid, and 0.12-12 kg/hectare of chlorogenic acid;

performing a fourth treatment during the fruiting period of the white kidney bean including spraying a third solution having 0.32-32 kg/hectare of salicylic acid, 0.32-32 kg/hectare of chlorogenic acid, and 1.2-49 kg/hectare of zinc sulfate; and performing a fifth treatment during the maturing period of the white kidney bean including spraying a fourth solution having 0.32-7.4 kg/hectare of salicylic acid and 0.32-7.4 kg/hectare of chlorogenic acid.

2. The method of claim 1, wherein preceding crops including potatoes, buckwheat, wheat, or corn may be planted before the preparing field.

3. The method of claim 1, wherein the seeds may be further exposed to the sun for 1 to 2 days before performing the first treatment.

4. The method of claim 1, wherein the amount of organic fertilizer applied to the field is approximately from 3 to 6 kg/m$^2$.

5. The method of claim 1, wherein the organic fertilizer is one or more selected from the group consisting of plant ash, compost, animal manure, and turf.

6. The method of claim 5, wherein the animal manure may further include cow manure, sheep manure, and chicken manure in a weight ratio of 5:3:2, and be mixed uniformly and matured for approximately from 60 to 120 days before use.

7. The method of claim 1, wherein the mass ratio of the seeds to the slurry is approximately from 1:0.1 to 0.8.

8. The method of claim 1, wherein the mass ratio of the seeds to the protective agent is approximately from 1:0.02 to 0.1.

9. The method of claim 1, wherein the slurry is one or more selected from the group consisting of albic soil, kaolin soil, yellow soil, red soil, and clay soil.

10. The method of claim 1, wherein the protective agent includes a wettable powder and a seed coating agent.

11. The method of claim 10, wherein the wettable powder and the seed coating agent are mixed in a mass ratio of 1:1 to 2.

12. The method of claim 10, wherein the wettable powder further includes a carrier and a supportive agent.

13. The method of claim 12, wherein the carrier is one or more selected from the group consisting of diatomaceous earth, pottery clay, kaolin clay, albic soil, peat, lightweight calcium carbonate, silica, and white carbon black.

14. The method of claim 12, wherein the supportive agent is one or more selected from the group consisting of saponin, anion surfactant, washing powder, sodium dodecyl sulfonate, sodium lignosulphonate, carboxymethyl cellulose, polyvinyl alcohol, polyethylene glycol, sodium tripolyphosphate, and sodium hexametaphosphate.

15. The method of claim 1, wherein the second solution may further include chromium (III) chloride having the concentration from 50 to 100 ppm.

16. The method of claim 1, wherein the third solution may further include chromium (III) chloride having the concentration from 50 to 100 ppm.

17. The method of claim 1, wherein the fourth solution may further include chromium (III) chloride having the concentration from 100 to 300 ppm.

18. A white kidney bean produced from claim 1, wherein the amount of the chromium content of the white kidney bean is from 400 to 800 µg/kg.

* * * * *